US00PP10854P

United States Patent [19]

Roberson

[11] Patent Number: Plant 10,854

[45] Date of Patent: Apr. 6, 1999

[54] LANTANA PLANT NAMED 'ROBPATCHE'

[76] Inventor: Robert J. Roberson, 31706 E. Pink Hill Rd., Grain Valley, Jackson County, Mo. 64029

[21] Appl. No.: 841,307

[22] Filed: Apr. 30, 1997

[51] Int. Cl.[6] ..... A01H 5/00

[52] U.S. Cl. ..... Plt./227

[58] Field of Search ..... Plt./54.1, 227

[56] References Cited

U.S. PATENT DOCUMENTS

P.P. 1,477 6/1955 Regan ..... Plt./54.1

P.P. 2,423 7/1964 Temple ..... Plt./54.1

*Primary Examiner*—Howard J. Locker

*Assistant Examiner*—Kent L. Bell

*Attorney, Agent, or Firm*—Rothwell, Figg, Ernst & Kurz

[57] ABSTRACT

This invention relates to a new and distinct *Lantana camara* cultivar which is outstanding because of its intense, cherry red color, very brief floret color transition periods, healthy & semi-compact mounding growth form, and dense forest green foliage.

1 Drawing Sheet

SUMMARY OF THE INVENTION

This invention relates to a new and distinct *Lantana camara* cultivar which is outstanding because of its intense, cherry red color, very brief floret color transition periods, healthy & semi-compact mounding growth form, and dense forest green foliage and primarily selected for these characteristics. This selection was made from a specially designed Lantana hybridizing program with said hybrid cultivars being planted and was grown in Grain Valley, Mo.

ORIGIN AND ASEXUAL REPRODUCTION

Asexual reproduction of this cultivar by tip cuttings was directed by me, such reproduction establishing that the plant does in fact maintain the characteristics described, in successive generations.

It should be noted that the plant was initally selected from a Lantana planting being grown near Grain Valley, Mo. in a cultivated area and has since been reproduced by tip cuttings in the vicinity of Grain Valley, Mo. with the new and distinct characteristics stated herein, found to be maintained through successive generations as before recited.

*Lantana camara* is native to the subtropics and tropical North and South America. They are woody ornamentals which are not usually winter hardy North of USDA horticulture Zone 9. The roughish leaves range from yellow-green to green to blue-green and the two basic growth forms are mounding and trailing (weeping). Bloom color usually include yellow, white, cream, pink, or orange.

The cultivar of *Lantana camara* 'Robpatche' may further be described as having a number of distinctive characteristics which are enumerated in the succeeding specific description but broadly stated as comprised of predominantly red floret clusters, very brief color-transition period, healthy growth habit, dense forest-green foliage, and semi-compact mounding form.

I have chosen to identify this new cultivar as *Lantana camara* 'Robpatche'. This cultivar is being marketed in the United States under the name of Patriot (tm) 'Cherry'.

BRIEF DESCRIPTION OF THE DRAWING

The accompanying photograph shows as nearly true as it is reasonably possible to make the same, in color illustrations of this character, typical leaves and flowers of the new variety. The photographic drawing illustrates the flower form, the distinctive color transitions of the florets, and the form and color of both bloom clusters and foliage.

In the drawing.

DETAILED DESCRIPTION

Figure 1:
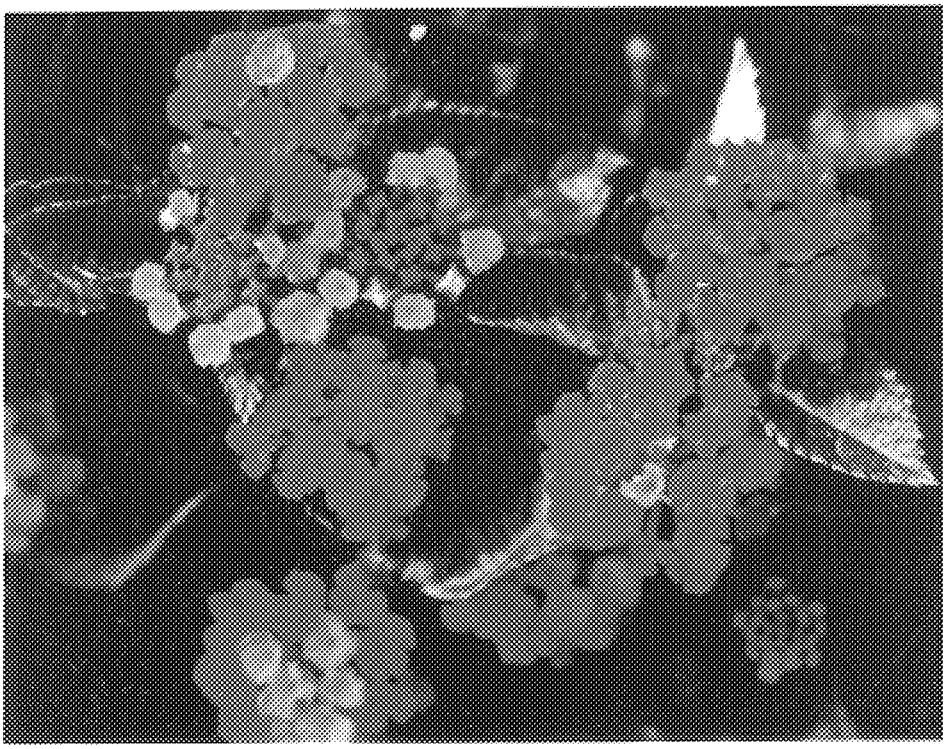
FIG. 1 illustrates the bloom cluster with varying maturity of the florets (to display the color range as well as possible) and the foliage.

In order to more specifically identify the cultivar, descriptive details are set forth hereinafter, along with related aspects of the plant which serve to distinguish the same, all colors being noted as compared with the Pantone Matching System (PMS). The measurements and colors were recorded from mature plants grown in the vicinity of Grain Valley, Mo.

Parentage:

*Seed Parent.*—*Lantana camara* 'Dallas Red' (unpatented).

*Pollen Parent.*—'Dallas Red' (unpatented); i.e. self-pollinated.

Propagation: Asexual reproduction by tip cuttings started near Grain Valley, Mo.

Plant descriptions:

*Inflorescence and reproductive parts.*—The inflorescence is a flat topped round cluster of 25–30 florets. The individual clusters are determinate and arise from the leaf axils. Each individual floret is slightly un-symmetrical with a bilateral symmetry and is subtended by a single bract. The perianth consist of: the Calyx (5 united sepals) and the Corolla (5 united petals with a narrow tube). The flowers are zygomorphic, hermaphroditic, and have 4 introse stamens which are didynamous. The ovary is superior, the style is terminal, and the stigma is lobed. The ovary is 2 locular, but is divided into 4 loculi by a false septum in each loculus. The placentation is axile with 2 ovules per carpel.

The fruit classification is drupe and potentially contains 2 seeds. When fruit forms, it is medium green (PMS#377); then matures through a darker green (PMS#385) to a near black (PMS#439).

Inflorescence dimensions:
*Bloom cluster.*—1.6" in diameter.
*Single Floret.*—0.3".
*Pedicle length.*—1.4".
*Corolla tube.*—0.5".
Inflorescence colors:
*Buds.*—Red (PMS#199).
*First opening.*—Yellow (PMS#121, briefly-24 hr.).
*Transitions through.*—Sienna (PMS#166- very briefly, 8–10 hr.).
*Maturity.*—Cherry Red (PMS#186).
*Tube.*—Cherry Red (PMS#186).
Developmental pattern: First flowers develop in a circular pattern on the periphery of the inflorescence.
Height and spread: In one growing season, i.e., frost to frost (May 5 to September 28, in USDA zone 5) 'Robpatche' reaches a height of 3 feet by 3 feet wide.
Plant vigor: Newly rooted (two week old) tip cuttings maintained in a greenhouse at 70° F. night temperature and 85° F. day temperature with 16 hour full sun days will result in an average growth of one inch per week.
Leaves and stems:
*Leaf shape.*—Ovate.
*Leaf Margins.*—Serrate.
*Leaf tip and base.*—Acute.
*Leaf veins.*—Pinnate.
*Leaf surface.*—Rough due to bristly hairs.
*Leaf arrangement.*—Opposite.
*Leaf color.*—Immature leaves are medium green (PMS#364) and mature leaves are forest green (PMS#357).
*Leaf size.*—Length 1⅞". Petiole 0.32". Width 1.1".
*Stem.*—Square in youth becoming round and woody with age.
Roots: Highly branched and fibrous
Flowering time: The color display begins blooming at 6–7 weeks after cuttings are made, or 4 weeks after potting, and continue until temperatures drop below 45 degrees Fahrenheit.
Diseases: No unusual susceptibility to diseases noted to date.
Insects: Typical of this plant genus, white flies can be attracted to Lantana. There are no other insect problems known at this time.

General Observations

*Lantana Camara.*—'Robpatche', with its intense cherry red florets, very brief floret color transition period, dense forest green foliage, healthy growth habit, and semi-compact mounding form is an excellent addition to the ornamental horticulture products offered.

For the purpose of ornamental horticulture in our present living environments which include smaller yard & patio gardening demands for more color, *Lantana camara* plant 'Robpatche' is ideal due to several characteristics:

A. It is an excellent plant for mass plantings, low borders, hanging baskets or floral specimen standards. *Lantana camara* 'Robpatche' will produce a continuous display of a bright, predominantly red color throughout the summer. This plant remains in bloom when most other flowering perennials' seasons have ended.
B. The healthy growth habit of this cultivar combined with its semi-compact mounding form make it ideal for today's demand for "instant" beauty and color as a ground cover, hedge, or specimen plant.
C. This cultivar offers a more consistently red bloom floret through its cycle than any other red Lantana, and produces blooms profusely and continually until temperatures drop below 45 degrees Fahrenheit.

Comparison to Known Varieties

*Lantana camara* plant 'Robpatche' should be compared with *Lantana camara* 'Dallas Red' as this is the nearest color comparison known in today's trade. The inflorescence form and color presentations of these two cultivars are somewhat similar.

A. Robpatche's very brief yellow and sienna transition periods, and its deeper cherry red (PMS#186) pigmentation at maturity, give an overall mass effect of a more homogenous and consistent red floret cluster display.
B. Though 'Dallas Red' florets open yellow and transition through sienna as does 'Robpatche', these color transitions extend for a longer period (44 hr. compared with 34 hr) than 'Robpatche' before reaching the mature floret color of fire engine red. This extended transition period gives a more multicolored effect in mass. 'Dallas Red' has a tendency to set seed more readily (30%) than that of 'Robpatche'.

I claim:

1. A new and distinct cultivar of *Lantana camara* plant substantially as illustrated and described.

* * * * *